(12) United States Patent
Kuo

(10) Patent No.: US 6,379,358 B1
(45) Date of Patent: Apr. 30, 2002

(54) CERVICAL CORRECTING BRACE

(76) Inventor: Robert W. H. Kuo, 3rd Fl., No. 1, Lane 43, Sec. 1, Chang-An E. Rd., Taipei (TW)

( * ) Notice: Subject to any disclaimer, the term of this patent is extended or adjusted under 35 U.S.C. 154(b) by 0 days.

(21) Appl. No.: 09/721,209

(22) Filed: Nov. 22, 2000

(51) Int. Cl.[7] .............................................. A61B 17/70
(52) U.S. Cl. ...................................................... 606/61
(58) Field of Search ............................ 606/53, 60, 61

(56) References Cited

U.S. PATENT DOCUMENTS

| | | | | |
|---|---|---|---|---|
| 4,686,970 A | * | 8/1987 | Dove et al. ................... | 606/61 |
| 4,738,251 A | * | 4/1988 | Plaza .......................... | 606/61 |
| 4,836,193 A | * | 6/1989 | Ransford ..................... | 606/61 |
| 4,841,959 A | * | 6/1989 | Ransford ..................... | 606/61 |
| 5,366,455 A | * | 11/1994 | Dove et al. ................... | 606/61 |
| 5,810,815 A | * | 9/1998 | Morales ....................... | 606/61 |

* cited by examiner

*Primary Examiner*—Paul J. Hirsch
(74) *Attorney, Agent, or Firm*—Alan Kamrath; Rider, Bennett, Egan & Arundel, LLP

(57) ABSTRACT

A cervical correction brace includes a pair of spaced upright bars each having a wavelike lower section and an inclined upper section. The upper sections extend upward and inward. A top crosspiece interconnects top ends of the upper sections.

6 Claims, 5 Drawing Sheets

CERVICAL CORRECTING BRACE

BACKGROUND OF THE INVENTION

1. Field of the Invention

The present invention relates to a cervical correcting brace and, more particularly, to a cervical correcting brace which can be securely attached to and provide long-term support for a cervical spine of a patient.

2. Description of Related Art

Many cervical braces are provided for treatment of defective spines. For example, FIG. 5 shows a cervical brace which includes a pair of spaced upright bars (30), each bar (30) having a straight lower section (31) and an inclined upper section (13) extending upward and forward from the lower section (31).

The cervical brace further includes a top crosspiece (34) interconnecting top ends of the upper sections (33) and a bottom crosspiece (32) interconnecting bottom ends of the lower sections (31) of the spaced bars (30), with each of the crosspieces (32, 34) being formed with a V-shaped portion (320, 340).

As shown in FIG. 6, the conventional cervical brace is applied to a patient's body by placing the lower sections (31) alongside a row of spinous processes of cervical vertebra, with the V-shaped portion (320) of the bottom crosspiece (32) engaging a cervical spine (20), and the V-shaped portion (340) of the top crosspiece (14) engaging the cranium (21) at its occipital. The conventional cervical brace must be fixed to the cervical spine (20) by winding a wire (22) round the top crosspiece (34) and the straight lower sections (31) of the bars (30), as well as round the cervical spine (20).

However, it has been found that this cervical brace might not remainsecurely attached to the cervical spine for sufficient time, since the wire (22) might slide over the straight lower sections (31) of the bars (30) and over the top crosspiece (34) inwardly, as denoted by opposite double arrows in FIG. 6, as a result of motion of the patient.

Therefore, it is an objective of the invention to provide a cervical correcting brace to mitigate and/or obviate the aforementioned problem.

SUMMARY OF THE INVENTION

The object of the present invention is to provide a cervical correcting brace which can be securely attached to a cervical spine of a patient.

Other objects, advantages and novel features of the invention will become more apparent from the following detailed description when taken in conjunction with the accompanying drawings.

DETAILED DESCRIPTION OF THE PREFERRED EMBODIMENT

Figures 1, 5:
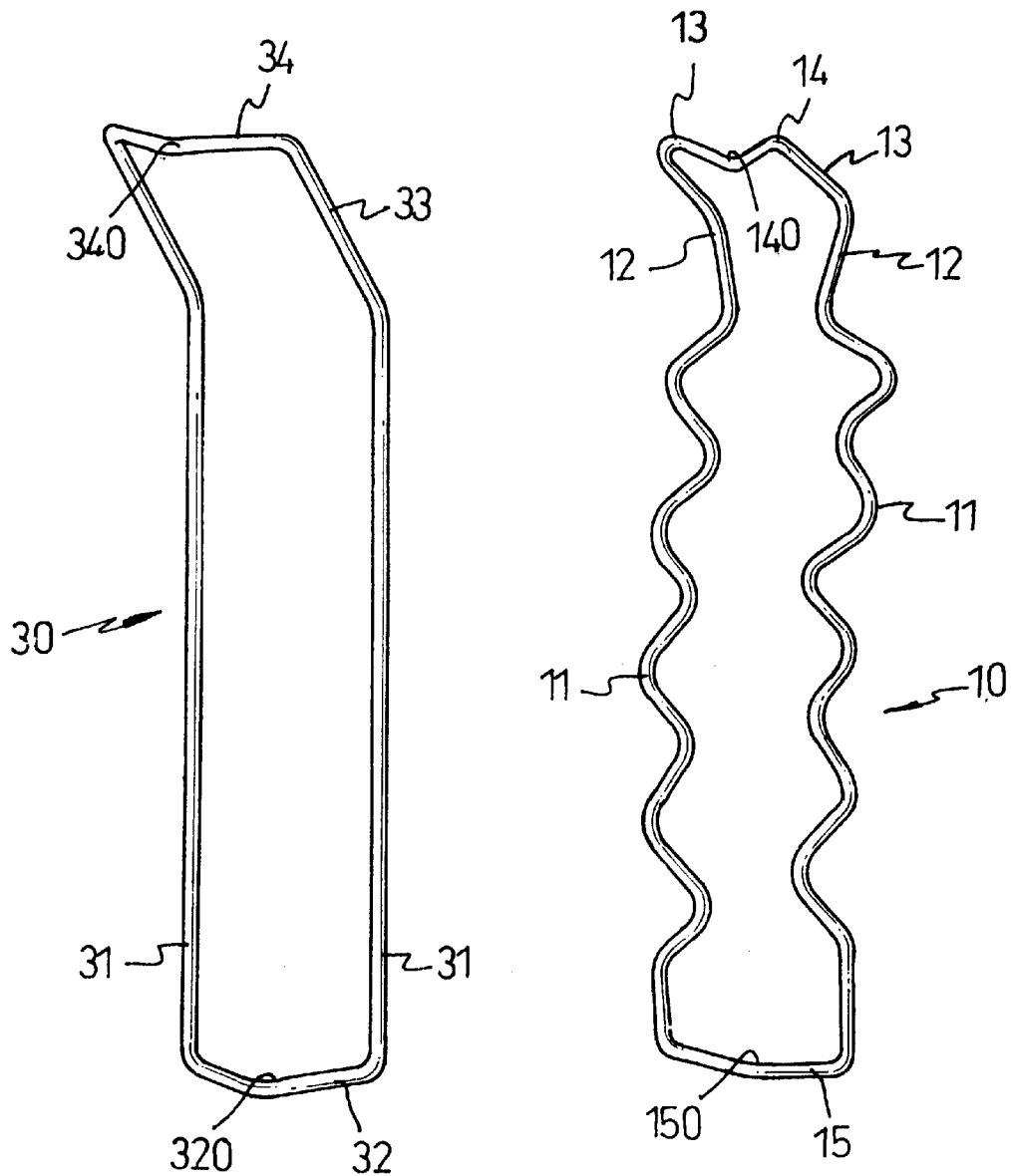
FIG. 1 is a perspective view of a preferred embodiment of a cervical correcting brace in accordance with the present invention.
FIG. 5 is a perspective view of a cervical brace of conventional type.
Figure 2:
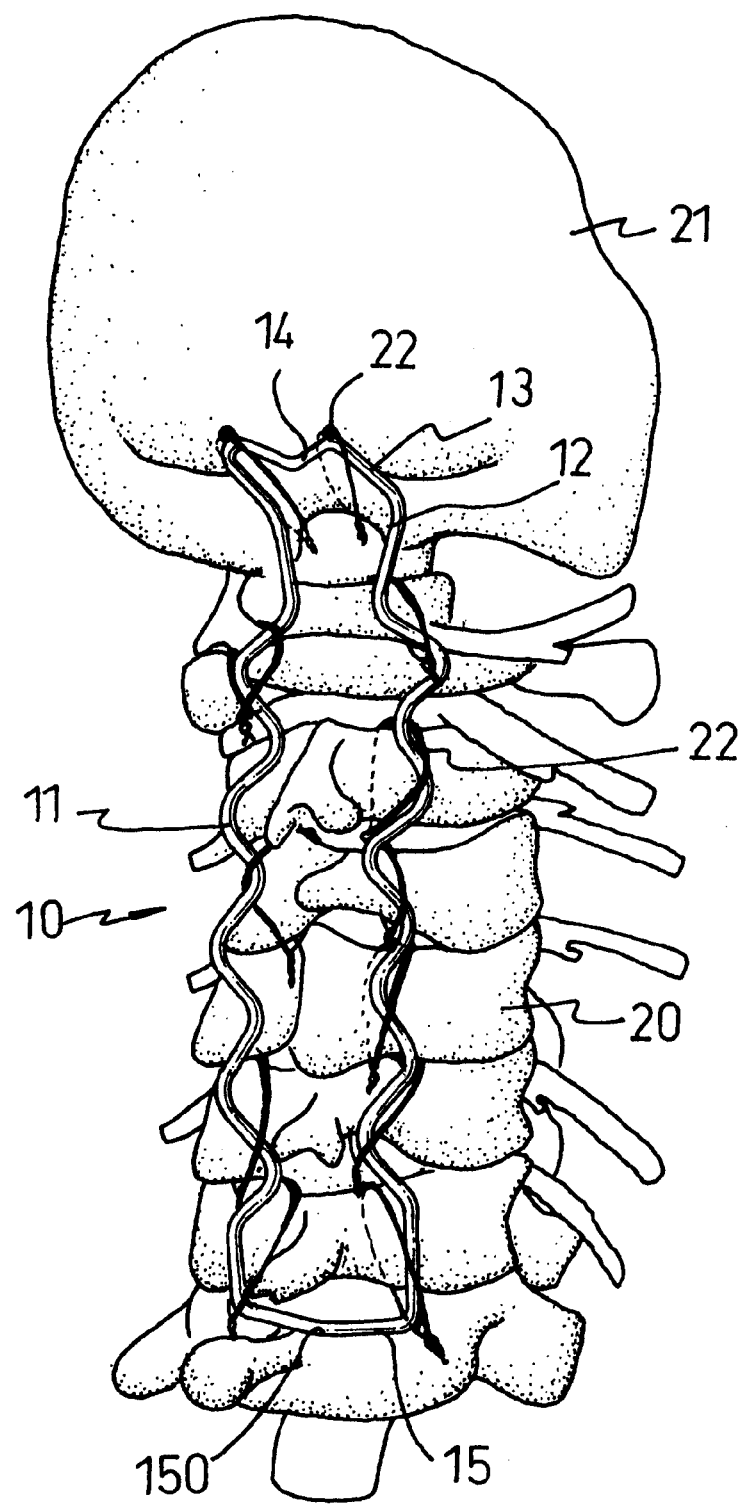
FIG. 2 is a perspective view showing the cervical brace of FIG. 1 in application.

FIGS. 1 and 2 show a cervical correcting brace in accordance with the present invention. The brace includes a pair of spaced upright bars (10), each having a wavelike lower section (11) and an inclined upper section (13), and preferably an intermediate section (12) formed between the lower and upper sections (11, 13). A top crosspiece (14) interconnects top ends of the inclined upper sections (13).

In a highly preferred embodiment, the cervical brace further includes a bottom crosspiece (15) that interconnects bottom ends of the lower sections (11) of the bars (10). Preferably, the bottom crosspiece (15) has an outwardly curved central portion (150) formed therein.

Figure 3:
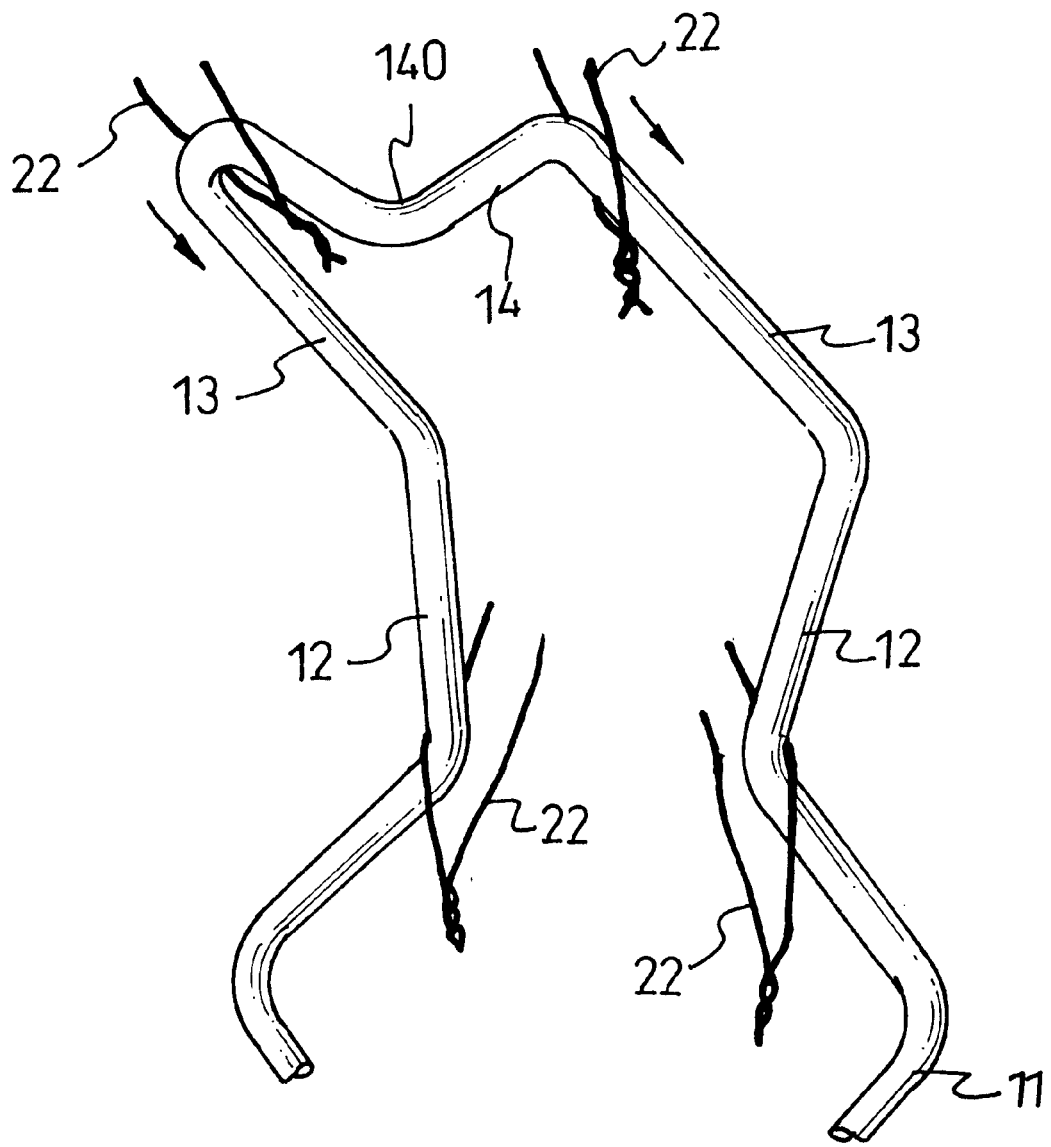
FIG. 3 is a fragmental enlarged perspective view of the cervical brace of FIG. 1.

Referring to FIG. 3, the upper sections (13) extend so as to define a forward inclined oblique plane that makes an angle with an upright plane defined by the two spaced lower sections (11). Additionally, the upper sections (13) extend upward and inward while the intermediate sections (12) extend upward but outward, if viewed from a site in front thereof.

Figure 4:
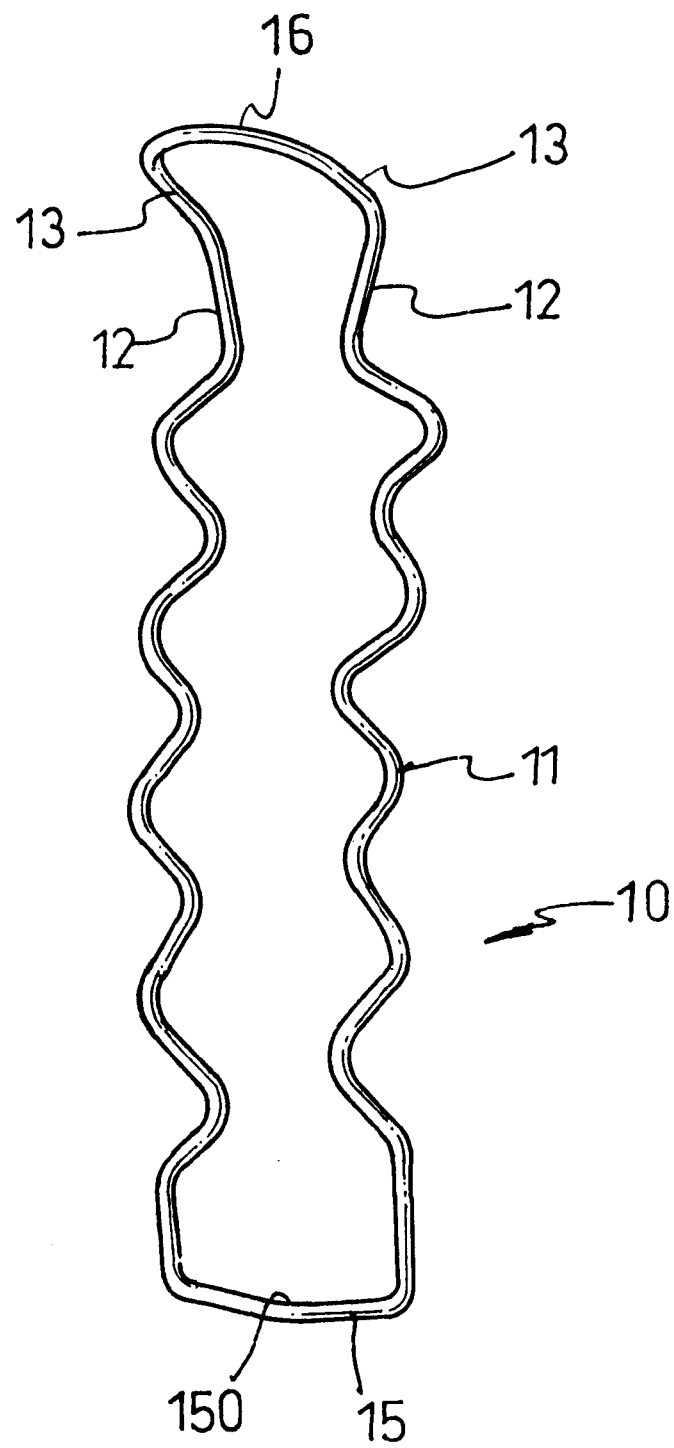
FIG. 4 is a perspective view of an alternative embodiment of the cervical brace in accordance with the present invention.
Figure 6:
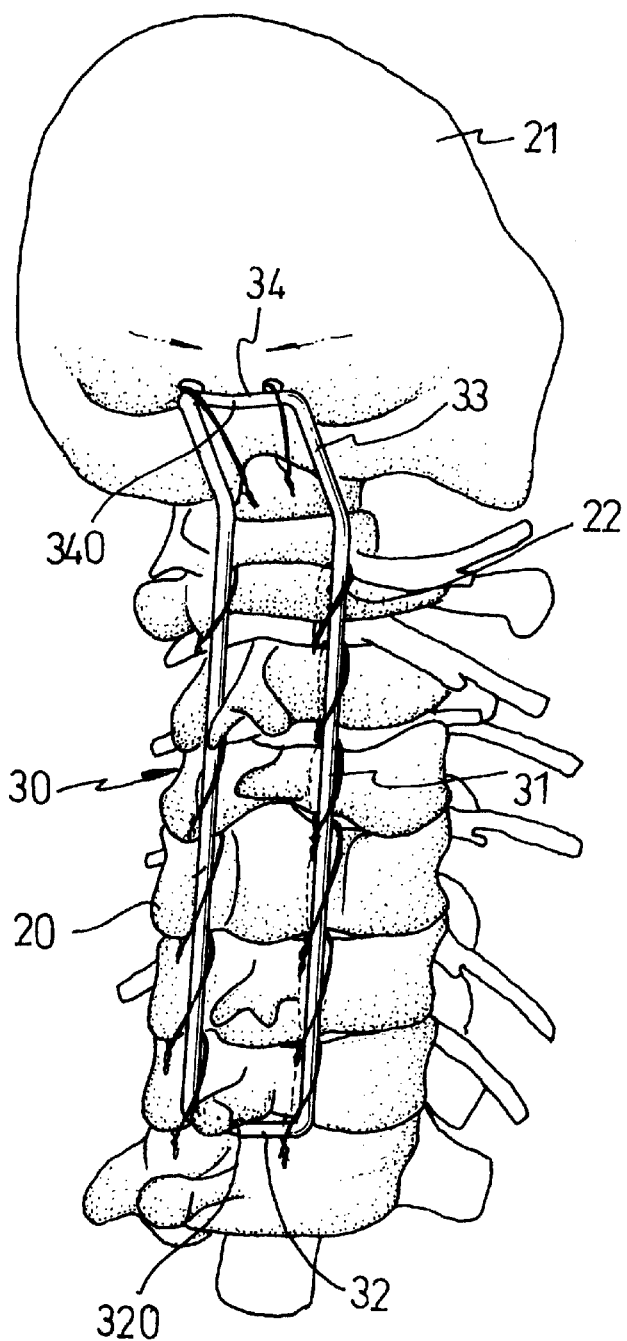
FIG. 6 is a perspective view showing the cervical brace of FIG. 5 in application.

The top crosspiece (14) may be formed with a V-shaped central portion (140), as shown in FIG. 3, or a curved portion (16), as shown in FIG. 4, that is contoured to support a cranium (21) at its occipital, as shown in FIG. 2.

Referring still to FIG. 2, the inventive cervical brace can be applied to a patient's body by placing the lower sections (11) alongside a row of spinous processes of vertebra, with the central portion (150) of the bottom crosspiece (15) snugly engaging the cervical spine (20), and with the V-shaped central portion (140) or the curved portion (16) of the top crosspiece (14) engaging the occipital and supporting the cranium (21).

The cervical brace is then fixed to the cervical spine (20) by winding a wire (22) round each lower section (11) at its wave crests and troughs and intersections of the upper sections (13) and the top crosspiece (14), as well as round the cervical spine (20). Consequently, the cervical spine (20) of the patient is kept straight.

From the above description, it is noted that the invention has the advantage that it can be securely attached to the cervical spine (20), since the wire (22) is wound at the above-mentioned wave crests and troughs and the intersections, which prevents the wire (22) from sliding over the sections (11, 12, 13) of the bars (10), whereby the patient's spine can be securely supported over a required length of time.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A cervical correcting brace for secure attachment by wire to a defective spine of a patient, whereby the cervical correcting brace securely supports the spine over a required length of time, the cervical correcting brace comprising:

a pair of upright bars (10) spaced apart from each other, each of said upright bars (10) having a wavelike lower section (11) and an inclined upper section (13), said upper section (13) extending upward and inward; and a top crosspiece (14) interconnecting top ends of each of said upper sections (13).

2. The cervical correcting brace as claimed in claim 1, wherein each of said upright bars (11) further has an intermediate section (12) formed between said lower section (11) and said upper section (13), and wherein said intermediate section (12) extends upward and outward.

3. The cervical correction brace as claimed in claim 1, wherein said top crosspiece (14) has a V-shaped portion (140) formed therein.

4. The cervical correction brace as claimed in claim 1, wherein said top crosspiece (14) has a curved portion (16) formed therein.

5. The cervical correction brace as claimed in claim 1 further including a bottom crosspiece (15) interconnecting the bottom ends of each of said lower sections (11).

6. The cervical correction brace as claimed in claim 5, wherein said bottom crosspiece (15) has an outwardly curved portion (150) formed therein.

* * * * *